(12) United States Patent
Grubbs et al.

(10) Patent No.: US 7,598,330 B2
(45) Date of Patent: Oct. 6, 2009

(54) CROSS-METATHESIS OF OLEFINS DIRECTLY SUBSTITUTED WITH AN ELECTRON-WITHDRAWING GROUP USING TRANSITION METAL CARBENE CATALYSTS

(75) Inventors: Robert H. Grubbs, South Pasadena, CA (US); John P. Morgan, Moosic, PA (US); Jennifer A. Love, Vancouver (CA); Tina M. Trnka, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 818 days.

(21) Appl. No.: 10/409,017

(22) Filed: Apr. 7, 2003

(65) Prior Publication Data

US 2003/0236427 A1 Dec. 25, 2003

Related U.S. Application Data

(60) Provisional application No. 60/370,308, filed on Apr. 5, 2002.

(51) Int. Cl.
*C08F 4/06* (2006.01)
*C07F 15/00* (2006.01)
*B01J 31/24* (2006.01)

(52) U.S. Cl. .................. 526/172; 526/336; 556/21; 556/22; 556/136; 502/152; 502/155

(58) Field of Classification Search ............... 526/172, 526/336; 502/192, 155; 556/21, 22, 136
See application file for complete search history.

(56) References Cited

U.S. PATENT DOCUMENTS

| | | | |
|---|---|---|---|
| 5,312,940 A | 5/1994 | Grubbs et al. |
| 5,342,909 A | 8/1994 | Grubbs et al. |
| 5,831,108 A | 11/1998 | Grubbs et al. |
| 5,969,170 A | 10/1999 | Grubbs et al. |
| 6,111,121 A | 8/2000 | Grubbs et al. |
| 6,211,391 B1 | 4/2001 | Grubbs et al. |
| 6,306,988 B1 | 10/2001 | Grubbs et al. |
| 2003/0100776 A1 | 5/2003 | Grubbs et al. |

FOREIGN PATENT DOCUMENTS

WO   WO 03/011455   2/2003

OTHER PUBLICATIONS

Collamn Principles and applications of Organotransition Metal Chemistry pp. 509 (1980).*
Sanford et al. (2001) J. Am Chem. Soc., 123:6543-6554,.*
Brümmer et al. (1997) "Olefin Cross-Metathesis with Monosubstituted Olefins," *Chem. Eur. J.* 3:441- 446.
Chatterjee et al. (2000), "Synthesis of Functionalized Olefins by Cross and Ring-Closing Metatheses," *J. Am. Chem. Soc.* 122(15):3783-3784.
Crowe et al. (1995) "Acrylonitrile Cross-Metathesis: Coaxing Olefin Metathesis Reactivity from a Reluctant Substrate," *J. Am. Chem. Soc.* 117:5162-5163.
Goldberg et al. (2002), "A One-Pot Cross-Metathesis/Allylboration Reaction: A Three-Component Coupling for the Synthesis of Functionalized Homoallylic Alcohols," *Angew. Chem. Int. Ed.* 41(5):807-810.
Itoh et al. (2000) "Synthesis of Bis- and Oligo-gem-difluorocyclopropanes Using the Olefin Metathesis Reaction," *Org. Lett.* 2:1431.
Toste et al. (2002), "Functional Group Diversity by Ruthenium-Catalyzed Olefin Cross-Metathesis," *Pure Appl. Chem.* 74(1):7-10.
Trnka et al. (2001), "The Development of $L_2X_2Ru=CHR$ Olefin Metathesis Catalysts: An Organometallic Success Story," *Accounts of Chemical Research* 34(1):18-29.
Wilhelm et al. (1997), "Reactivity of $Ru(H)(H_2)Cl(PCy_3)_2$ with Propargyl and Vinyl Chlorides: New Methodology to Give Metathesis-Active Ruthenium Carbenes," *Organometallics* 16(18):3867-3869.
Blanco et al., (1999) "New results on the functionalization of terminal alkenes by cross-metathesis reactions," *Synlett*, 5:557-558.
Chatterjee et al., (1999) "Synthesis of trisubstituted alkenes via olefin cross-metathesis," *Org. Lett.* 1(11):1751-1753.
Love et al, (2002) "A practical and highly active ruthenium-based catalyst that effects the cross metathesis of acrylonitrile," *Angew. Chem. Int. Ed.* 41(21):4035-4037.
Sanford et al., "Mechanism and activity of ruthenium olefin metathesis catalysts," J. Am: Chem. Soc., 2001, 123:6543-6554.

* cited by examiner

*Primary Examiner*—Janet L. Andres
*Assistant Examiner*—Raymond Covington

(57) ABSTRACT

The invention pertains to the use of Group 8 transition metal alkylidene complexes as catalysts for olefin cross-metathesis reactions. In particular, ruthenium and osmium alkylidene complexes substituted with an N-heterocyclic carbene ligand and at least one electron donor ligand in the form of a heterocyclic group are used to catalyze cross-metathesis reactions to provide a olefin products that are directly substituted with an electron-withdrawing group.

43 Claims, No Drawings

CROSS-METATHESIS OF OLEFINS DIRECTLY SUBSTITUTED WITH AN ELECTRON-WITHDRAWING GROUP USING TRANSITION METAL CARBENE CATALYSTS

CROSS-REFERENCE TO RELATED APPLICATIONS

This application claims priority under 35 U.S.C. §119(e)(1) to provisional U.S. patent application Ser. No. 60/370,308, filed Apr. 5, 2002, the disclosure of which is incorporated by reference in its entirety.

TECHNICAL FIELD

This invention relates generally to a method for carrying out an olefin metathesis reaction using a Group 8 transition metal complex as a catalyst, and more particularly relates to a method for carrying out cross-metathesis reactions using such a catalyst. The invention enables the synthesis of olefins that are directly substituted with an electron-withdrawing group via a cross-metathesis reaction. as reactants to synthesize acrylonitriles as reactants to synthesize disubstituted cyano-olefins. The invention has utility in the fields of catalysis, organic synthesis, and organometallic chemistry.

BACKGROUND OF THE INVENTION

To the synthetic organic or polymer chemist, simple methods for forming carbon-carbon bonds are extremely important and valuable tools. One method of C—C bond formation that has proved particularly useful is transition-metal catalyzed olefin metathesis. "Olefin metathesis," as is understood in the art, refers to the metal-catalyzed redistribution of carbon-carbon bonds. See Trnka and Grubbs (2001) *Acc. Chem. Res.* 34:18-29. Over two decades of intensive research effort has culminated in the discovery of well-defined transition metal alkylidene complexes that are highly active olefin metathesis catalysts and stable in the presence of a variety of functional groups.

Examples of these transition metal alkylidene complexes are described in U.S. Pat. Nos. 5,312,940, 5,342,909, 5,831,108, 5,969,170, 6,111,121, and 6,211,391 to Grubbs et al., assigned to the California Institute of Technology. The complexes disclosed in these patents all possess metal centers that are formally in the +2 oxidation state, have an electron count of 16, and are penta-coordinated. These catalysts are of the general formula XX'M(LL')=CRR' wherein M is a Group 8 transition metal such as ruthenium or osmium, X and X' are anionic ligands, L and L' are neutral electron donors, and R and R' are specific substituents, e.g., one may be H and the other may be a substituted or unsubstituted hydrocarbyl group such as phenyl or C=C(CH$_3$)$_2$. Such complexes have been disclosed as useful in catalyzing a variety of olefin metathesis reactions, including ring-opening metathesis polymerization ("ROMP"), ring closing metathesis ("RCM"), acyclic diene metathesis polymerization ("ADMET"), ring-opening metathesis ("ROM"), and cross-metathesis ("CM" or "XMET") reactions.

Such metathesis catalysts include those that have been prepared with phosphine ligands, e.g., triphenylphosphine or dimethylphenylphospine, exemplified by phenylmethylenebis(tricyclohexylphosphine)ruthenium dichloride

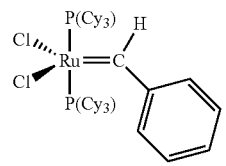

wherein "Cy" is cyclohexyl. See U.S. Pat. No. 5,917,071 to Grubbs et al. and Trnka and Grubbs (2001), cited supra. These compounds are highly reactive catalysts useful for catalyzing a variety of olefin metathesis reactions, and are tolerant of many different functional groups. See Schwab et al. (1995) *Angew. Chem, Int. Ed. Engl.* 34:2039-2041 and Schwab et al. (1996) *J. Am. Chem. Soc.* 118:100-110. However, as has been recognized by those in the field, the compounds display low thermal stability, decomposing at relatively low temperatures. Jafarpour and Nolan (2000) *Organometallics* 19(11):2055-2057.

More recently, significant interest has focused on such transition metal alkylidene catalysts wherein one of the phosphine ligands is replaced with an N-heterocyclic carbene ligand. See, e.g., Trnka and Grubbs, supra; Bourissou et al. (2000) *Chem. Rev.* 100:39-91; Scholl et al. (1999) *Tetrahedron Lett.* 40:2247-2250; Scholl et al. (1999) *Organic Lett.* 1(6):953-956; and Huang et al. (1999) *J. Am. Chem. Soc.* 121:2674-2678. N-heterocyclic carbene ligands offer many advantages, including readily tunable steric bulk, vastly increased electron donor character, compatibility with a variety of metal species, and improved thermal stability. See Scholl et al. (1999) *Tetrahedron Lett.* 40:2247-2250; Scholl et al. (1999) *Org. Lett.* 1:953-956; Chatterjee et al. (2000) *J. Am. Chem. Soc.* 122:3783-3784; and Bielawski et al. (2000) *Angew. Chem. Int. Ed.* 39:2903-2906, A representative of these second generation catalysts is the ruthenium complex (IMesH$_2$)(PCy$_3$)(Cl)$_2$Ru=CHPh

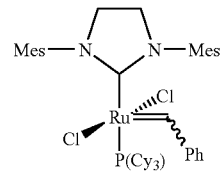

wherein Cy is cyclohexyl, Ph is phenyl, and Mes represents mesityl (2,4,6-trimethylphenyl).

These transition metal carbene complexes have been found to address a number of previously unsolved problems in olefin metathesis reactions, particularly cross-metathesis reactions. However, metathesis reactions with directly functionalized olefins, particularly olefins that are directly substituted with an electron-withdrawing substituent, remain a formidable challenge.

For example, acrylonitriles are unusually difficult substrates to use in olefin metathesis reactions, and only one single-component catalyst system, based on molybdenum, has been described as active for cyano-olefin cross-metathesis (Crowe et al. (1995) *J. Am. Chem. Soc.* 117:5162-5163; Brümmer et al. (1997) *Chem. Eur. J.* 3:441-446). This is in part due to the fact that these olefins are directly substituted with an electron-withdrawing group, and in part a result of the metal-coordinating ability of the cyano group. See Randl et al. (2001) *Synlett,* pp. 430-432, Blanco et al. (1999) *Synlett,* pp. 557-558, Gessler et al. (2000) *Tetrahedron Lett.* 41:9973-9976, and Cossy et al. (2001) *J. Organomet. Chem.* 634:216-221.

Accordingly, there is a need in the art for an effective and efficient method of carrying out an olefin metathesis reaction using olefins substituted with an electron-withdrawing group, e.g., a cyano-substituted olefin.

SUMMARY OF THE INVENTION

The present invention is addressed to the aforementioned needs in the art, and provides a novel process for using certain Group 8 transition metal complexes to catalyze olefin metathesis reactions, primarily cross-metathesis reactions, wherein the olefins are substituted with an electron-withdrawing group. The complexes used are metal alkylidene complexes comprised of a Group 8 transition metal, e.g., ruthenium or osmium. These complexes contain, in addition to the functional alkylidene ligand, two anionic ligands and two or three neutral electron donor ligands. One of the neutral electron donor ligands is strongly binding, i.e., selected so as to remain bound to the metal center of the complex throughout the metathesis reaction, while the remaining neutral electron donor ligand(s) are more weakly binding, and thus dissociate from the metal center during reaction, prior to olefin binding. In contrast to previous catalysts used in olefin cross-metathesis, the present complexes allow an olefinic reactant to be substituted with an electron-withdrawing group without significantly compromising the efficiency or selectivity of a metathesis reaction involving that olefin.

These cross-metathesis reactions are carried out with a catalyst having the structure of formula (I)

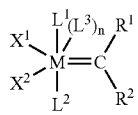
(I)

in which:
$L^1$ is a strongly coordinating neutral electron donor ligand;
n is zero or 1;
$L^2$ and $L^3$ are weakly coordinating neutral electron donor ligands;
$X^1$ and $X^2$ are anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, and functional groups, or may be taken together to form a vinylidene moiety,
wherein any two or more of $X^1$, $X^2$, $L^1$, $L^2$, $L^3$, $R^1$, and $R^2$ can be taken together to form a cyclic group, and further wherein any one or more of $X^1$, $X^2$, $L^1$, $L^2$, $L^3$, $R^1$, and $R^2$ may be attached to a support.

Preferred catalysts contain Ru or Os as the Group 8 transition metal, with Ru particularly preferred.

The metal centers of these complexes are formally in the +2 oxidation state. It will be appreciated that when n is zero, the metal center has an electron count of 16 and is penta-coordinated, while when n is 1, the metal center has an electron count of 18 and is hexacoordinated. The complexes may also be modified so as to be cationic (in which case one of the anionic ligands dissociates), such that the metal center has an electron count of 14 and is tetracoordinated. These complexes are represented by structures (II), (III), and (IV), respectively:

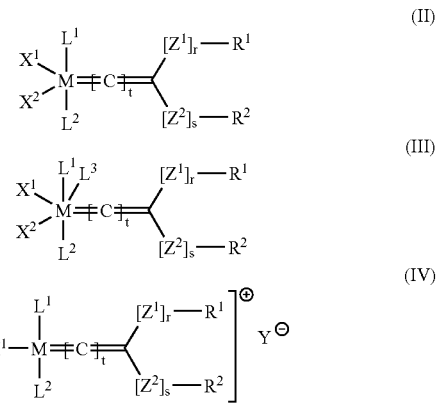

In the foregoing structures, $X^1$, $X^2$, $L^1$, $L^2$, $L^3$, $R^1$, and $R^2$ are as defined previously, r and s are independently zero or 1, t is an integer in the range of zero to 5, Y is any noncoordinating anion, $Z^1$ and $Z^2$ are linkages containing 1 to about 6 spacer atoms, any two or more of $X^1$, $X^2$, $L^1$, $L^2$, $L^3$, $Z^1$, $Z^2$, $R^1$, and $R^2$ may be taken together to form a cyclic group, e.g., a multidentate ligand, and any one or more of $X^1$, $X^2$, $L^1$, $L^2$, $L^3$, $Z^1$, $Z^2$, $R^1$, and $R^2$ may be attached to a support.

Exemplary catalysts are transition metal carbene complexes wherein $L^2$ and $L^3$ are optionally substituted heterocyclic ligands and $L^1$ is a carbene having the structure of formula (V)

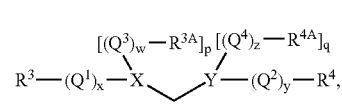
(V)

such that the complex has the structure of formula (VI)

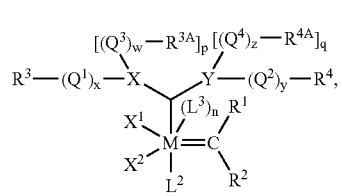
(VI)

wherein:
$X^1$, $X^2$, $L^1$, $L^2$, $L^3$, n, $R^1$, and $R^2$ are as defined above;
X and Y are heteroatoms selected from N, O, S, and P;
p is zero when X is O or S, and p is 1 when X is N or P;
q is zero when Y is O or S, and q is 1 when Y is N or P;
$Q^1$, $Q^2$, $Q^3$, and $Q^4$ are independently selected from hydrocarbylene, substituted hydrocarbylene, heteroatom-containing hydrocarbylene, substituted heteroatom-containing hydrocarbylene, and —(CO)—, and further wherein two or more substituents on adjacent atoms within Q may be linked to form an additional cyclic group;
w, x, y, and z are independently zero or 1; and
$R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl, wherein any two or more of $X^1$, $X^2$, $L^2$, $L^3$, $R^1$, $R^2$, $R^3$, $R^{3A}$, $R^4$, and $R^{4A}$ can be taken together to form a cyclic group, and further wherein any one or more of $X^1$, $X^2$, $L^2$, $L^3$, $R^1$, $R^2$, $R^3$, $R^{3A}$, $R^4$, and $R^{4A}$ may be attached to a support.

In a preferred embodiment, $L^1$ is an N-heterocyclic carbene having the structure of formula (VII)

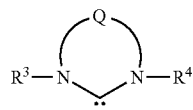

(VII)

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage.

A preferred metal carbene complex of formula (VI) is a ruthenium complex having the structure of formula (VIII)

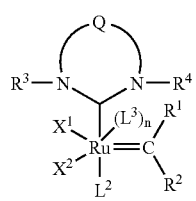

(VIII)

wherein $X^1$, $X^2$, $L^1$, $L^2$, $L^3$, n, Q, $R^1$, $R^2$, $R^3$, and $R^4$ are as defined previously.

In one embodiment, then, a method is provided for synthesizing an olefin that is substituted with an electron-withdrawing group and at least one other substituent, wherein the electron-withdrawing group is directly bound to an olefinic carbon atom. The method involves using a transition metal carbene complex as described above to catalyze a cross-metathesis reaction between two olefinic reactants, or "cross partners," wherein at least one of the olefinic reactants is directly substituted with an electron-withdrawing group E. Generally, such reactants have the structure of formula (IX)

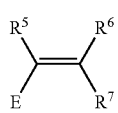

(IX)

wherein:

E is the electron-withdrawing group;

$R^5$, $R^6$, and $R^7$ are independently selected from the group consisting of hydrogen, -$(Z)_m$-Fn, hydrocarbyl, substituted hydrocarbyl, heteroatom-containing hydrocarbyl, and substituted heteroatom-containing hydrocarbyl, and, if substituted hydrocarbyl or substituted heteroatom-containing hydrocarbyl, wherein one or more of the substituents may be -$(Z)_n$-Fn;

Fn is a functional group;

m is zero or 1; and

Z is a hydrocarbylene or a substituted and/or heteroatom-containing hydrocarbylene linking group such as an alkylene, substituted alkylene, heteroalkylene, substituted heteroalkene, arylene, substituted arylene, heteroarylene, or substituted heteroarylene linkage The reaction partner, i.e., the second olefinic reactant, has a molecular structure given by formula (X)

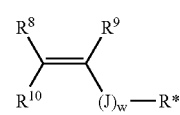

(X)

wherein w is zero or 1, J is a linking group, R* is a nonhydrogen substituent, e.g., hydrocarbyl, substituted hydrocarbyl, heteroatom-containing hydrocarbyl, substituted heteroatom-containing hydrocarbyl, or Fn, and $R^8$, $R^9$, and $R^{10}$ are hydrogen, hydrocarbyl, substituted hydrocarbyl, heteroatom-containing hydrocarbyl, substituted heteroatom-containing hydrocarbyl, -$(Z)_m$-Fn, or -$(J)_w$-R*.

DETAILED DESCRIPTION OF THE INVENTION

I. Definitions and Nomenclature

It is to be understood that unless otherwise indicated this invention is not limited to specific reactants, reaction conditions, ligands, or the like, as such may vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a compound" encompasses a combination or mixture of different compounds as well as a single compound, reference to "a substituent" includes a single substituent as well as two or more substituents that may or may not be the same, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a linear, branched, or cyclic saturated hydrocarbon group typically although not necessarily containing 1 to about 20 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 20 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 20 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl"; include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctyl-naphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined. The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The term "cyclic" refers to alicyclic or aromatic substituents that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" are used in the conventional sense to refer to a chloro, bromo, fluoro or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl."

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{20}$ alkoxy, $C_2$-$C_{20}$ alkenyloxy, $C_2$-$C_{20}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{20}$ alkylcarbonyl (—CO-alkyl) and $C_6$-$C_{24}$ arylcarbonyl (—CO-aryl)), acyloxy (—O-acyl, including $C_2$-$C_{20}$ alkylcarbonyloxy (—O—CO-alkyl) and $C_6$-$C_{24}$ arylcarbonyloxy (—O—CO-aryl)), $C_2$-$C_{20}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{20}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH$_2$), mono-($C_1$-$C_{20}$ alkyl)-substituted carbarmoyl (—(CO)13NH($C_1$-$C_{20}$ alkyl)), di-($C_1$-$C_{20}$ alkyl)-substituted carbamoyl (—(CO)—N($C_1$-$C_{20}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{20}$ alkyl), N—($C_5$-$C_{24}$ aryl)-substituted carbamoyl, thiocarbamoyl (—(CS)—NH$_2$), mono-($C_1$-$C_{20}$ alkyl)-substituted thiocarbamoyl (—(CO)—NH($C_1$-$C_{20}$ alkyl)), di-($C_1$-$C_{20}$ alkyl)-substituted thiocarbamoyl (—(CO)—N($C_1$-$C_{20}$ alkyl)$_2$), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{20}$ alkyl), N—($C_1$-$C_{24}$ aryl)-substituted thiocarbamoyl, carbamido (—NH—(CO)—NH$_2$), cyano(—C≡N), cyanato (—O—C≡N), thiocyanato (—S—C≡N), formyl (—(CO)—H), thioformyl (—(CS)—H), amino (—NH$_2$), mono-($C_1$-$C_{20}$ alkyl)-substituted amino, di-($C_1$-$C_{20}$ alkyl)-substituted amino, mono-($C_5$-$C_{24}$ aryl)-substituted amino, di-($C_5$-$C_{24}$ aryl)-substituted amino, $C_2$-$C_{20}$ alkylamido (—NH—(CO)-alkyl), $C_6$-$C_{24}$ arylamido (—NH—(CO)-aryl), imino (—CR═NH where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR═N(alkyl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), arylimino (—CR═N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^{31}$), $C_1$-$C_{20}$ alkylsulfanyl (—S-alkyl; also termed "alkylthio"), $C_5$-$C_{24}$ arylsulfanyl (—S-aryl; also termed "arylthio"), $C_1$-$C_{20}$ alkylsulfinyl (—(SO)-alkyl), $C_5$-$C_{24}$arylsulfinyl (—(SO)-aryl), $C_1$-$C_{20}$ alkylsulfonyl (—SO$_2$-alkyl), $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{20}$ alkyl (preferably $C_1$-$C_{12}$ alkyl, more preferably $C_1$-$C_6$ alkyl), $C_2$-$C_{20}$ alkenyl (preferably $C_2$-$C_{12}$ alkenyl, more preferably $C_2$-$C_6$ alkenyl), $C_2$-$C_{20}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

II. The Catalyst

The cross-metathesis reactions of the invention are carried out catalytically, using a Group 8 transition metal complex having the structure of formula (I)

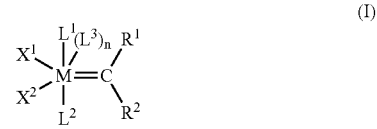

(I)

in which the various substituents are as follows.

M, which serves as the transition metal center in the +2 oxidation state, is a Group 8 transition metal, particularly ruthenium or osmium. In a particularly preferred embodiment, M is ruthenium.

$L^1$ is a strongly coordinating neutral electron donor ligand, as will be discussed in detail infra.

$L^2$ and $L^3$ are weakly coordinating neutral electron donor ligands in the form of optionally substituted heterocyclic groups, and n is zero or 1, such that $L^3$ may or may not be present. Generally, $L^2$ and $L^3$ are optionally substituted five- or six-membered monocyclic groups containing 1 to 4, preferably 1 to 3, most preferably 1 to 2 heteroatoms, or are optionally substituted bicyclic or polycylic structures composed of 2 to 5 such five- or six-membered monocyclic groups. If the heterocyclic group is substituted, it should not be substituted on a coordinating heteroatom, and any one cyclic moiety within a heterocyclic group will generally not be substituted with more than 3 substituents. Examples of $L^2$ and $L^3$ include, without limitation:

nitrogen-containing heterocycles such as pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole;

sulfur-containing heterocycles such as thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene;

oxygen-containing heterocycles such as 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran; and mixed heterocycles such as isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine.

Preferred $L^2$ and $L^3$ ligands are aromatic nitrogen-containing and oxygen-containing heterocycles, and particularly preferred $L^2$ and $L^3$ ligands are monocyclic N-heteroaryl ligands that are optionally substituted with 1 to 3, preferably 1 or 2, substituents. Specific examples of particularly preferred $L^2$ and $L^3$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on $L^2$ and/or $L^3$ are selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, $C_6$-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_5$-$C_{24}$ aryl)-substituted carbamoyl, mono-($C_1$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$ alkyl)-substituted amino, mono-($C_1$-$C_{24}$ aryl)-substituted amino, di-($C_5$-$C_{24}$ aryl)-substituted amino, di-N—($C_1$-$C_{20}$ alkyl), N—($C_5$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on $L^2$ and $L^3$ include, without limitation, halo, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroaralkyl, $C_1$-$C_{12}$ alkoxy, $C_5$-$C_{14}$ aryloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_{14}$ aryl)-substituted amino, and nitro.

Of the foregoing, the most preferred substituents are halo, $C_1$-$C_6$ alkyl, $C_1$-$C_6$ haloalkyl, $C_1$-$C_6$ alkoxy, phenyl, substituted phenyl, formyl, N,N-di$C_1$-$C_6$ alkyl)amino, nitro, and nitrogen heterocycles as described above (including, for example, pyrrolidine, piperidine, piperazine, pyrazine, pyrimidine, pyridine, pyridazine, etc.).

$L^2$ and $L^3$ may also be taken together to form a bidentate or multidentate ligand containing two or more, generally two, coordinating heteroatoms such as N, O, S, or P, with preferred such ligands being diimine ligands of the Brookhart type. One representative bidentate ligand has the structure of formula (XI)

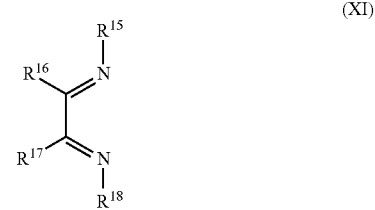

wherein $R^{15}$, $R^{16}$, $R^{17}$, and $R^{18}$ hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), heteroatom-containing hydrocarbyl (e.g., $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or substituted heteroatom-containing hydrocarbyl (e.g., substituted $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or (1) $R^{15}$ and $R^{16}$, (2) $R^{17}$ and $R^{18}$, (3) $R^{16}$ and $R^{17}$, or (4) both $R^{15}$ and $R^{16}$, and $R^{17}$ and $R^{18}$, may be taken together to form a ring, i.e., an N-heterocycle. Preferred cyclic groups in such a case are five-and six-membered rings, typically aromatic rings.

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl; $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments, $X^1$ and $X^2$ are each chloride.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5 to 8, ring atoms. $R^1$ and $R^2$ may also together form a vinylidene moiety or an analog thereof, as discussed infra with respect to catalysts having the structure of formula (II), (III), and (IV).

In preferred catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined earlier herein. Most preferably, $R^2$ is phenyl or vinyl substituted with one or more moieties selected from methyl, ethyl, chloro, bromo, iodo, fluoro, nitro, dimethylamino, methyl, methoxy, and phenyl. Optimally, $R^2$ is phenyl or $-C=C(CH_3)_2$.

Any two or more (typically two, three, or four) of $X^1$, $X^2$, $L^1$, $L^2$, $L^3$, $R^1$, and $R^2$ can be taken together to form a cyclic group, as disclosed, for example, in U.S. Pat. No. 5,312,940 to Grubbs et al. When any of $X^1$, $X^2$, $L^1$, $L^2$, $L^3$, $R^1$, and $R^2$ are linked to form cyclic groups, those cyclic groups may be five- or six-membered rings, or may comprise two or three five- or six-membered rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

In preferred catalysts, $L^1$ is a carbene ligand having the structure of formula (V)

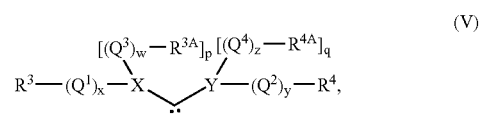

(V)

such that the complex has the structure of formula (VI)

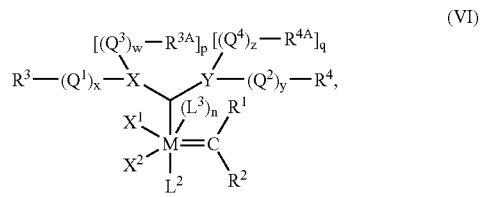

(VI)

wherein $X^1$, $X^2$, $L^1$, $L^2$, $L^3$, n, $R^1$, and $R^2$ are as defined previously, and the remaining substituents are as follows:

X and Y are heteroatoms typically selected from N, O, S, and P. Since O and S are divalent, p is necessarily zero when X is O or S, and q is necessarily zero when Y is O or S. However, when X is N or P, then p is 1, and when Y is N or P, then q is 1. In a preferred embodiment, both X and Y are N.

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Preferably, w, x, y, and z are all zero. Further, two or more substituents on adjacent atoms within Q may be linked to form an additional cyclic group.

$R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl.

In addition, any two or more of $X^1$, $X^2$, $L^1$, $L^2$, $L^3$, $R^1$, $R^2$, $R^3$, $R^{3A}$, $R^4$, and $R^{4A}$ can be taken together to form a cyclic group, and any one or more of $X^1$, $X^2$, $L^1$, $L^2$, $L^3$, $R^1$, $R^2$, $R^3$, $R^{3A}$, $R^4$, and $R^{4A}$ may be attached to a support.

Preferably, $R^{3A}$ and $R^{4A}$ are linked to form a cyclic group so that the carbene ligand has the structure of formula (VII)

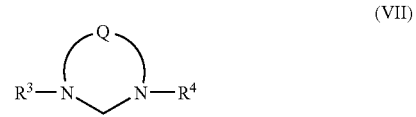

(VII)

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage.

Examples of N-heterocyclic carbene ligands suitable as $L^1$ thus include, but are not the following:

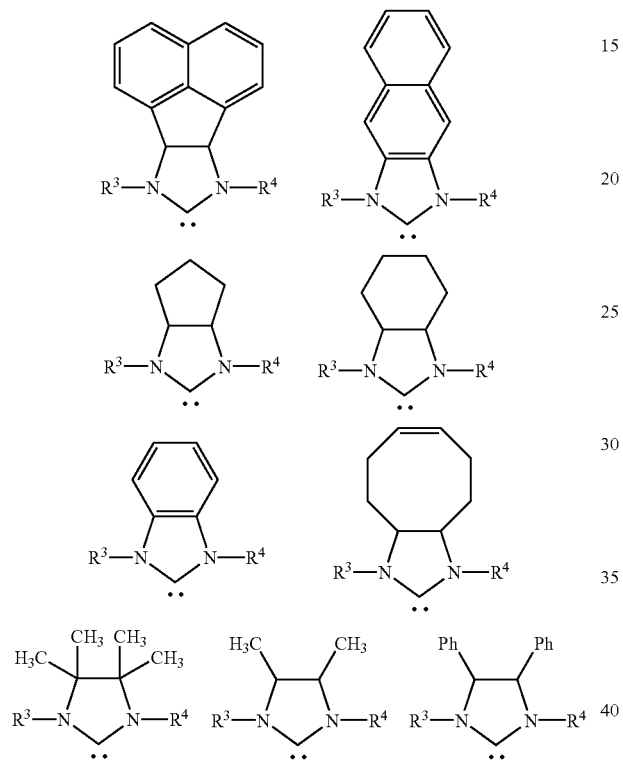

When M is ruthenium, then, the preferred complexes have the structure of formula (VIII)

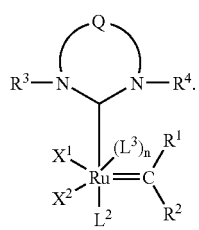

(VIII)

In a more preferred embodiment, Q is a two-atom linkage having the structure
—$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of functional groups here include carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents.

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. More preferably, $R^3$ and $R^4$ are mesityl.

Examples of such catalysts include, but are not limited to, the following:

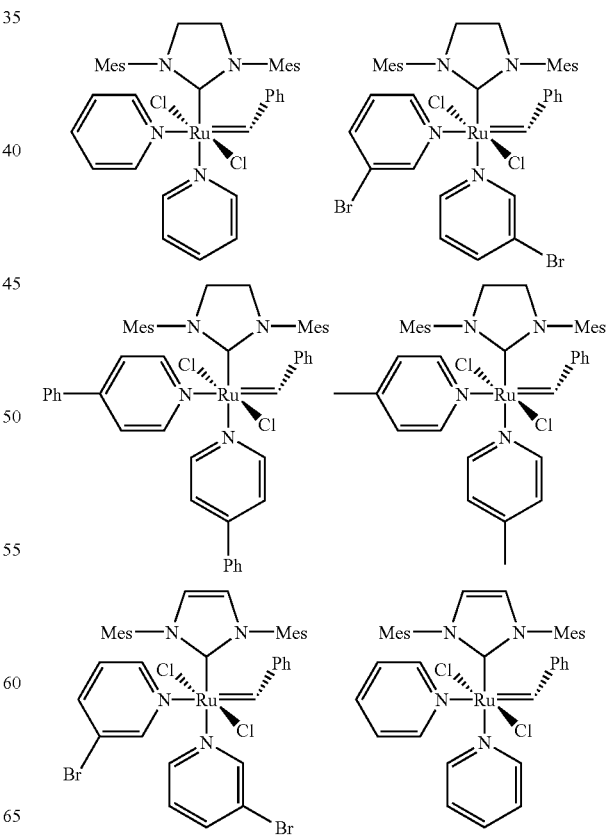

-continued

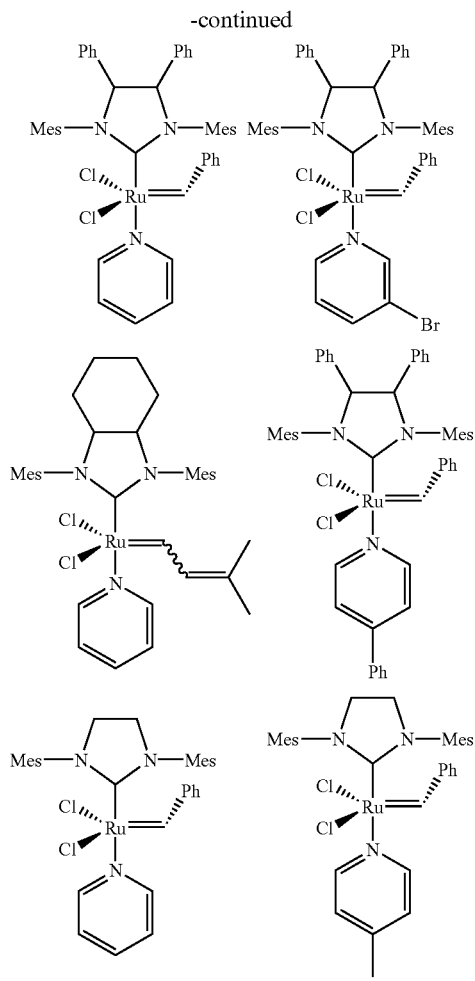

In the foregoing molecular structures, Ph represents phenyl, and Mes represents mesityl.

Additional transition metal carbene complexes include, but are not limited to:

neutral ruthenium or osmium metal carbene complexes containing metal centers that are formally in the +2 oxidation state, have an electron count of 16, are penta-coordinated, and are of the general formula (II);

cationic ruthenium or osmium metal carbene complexes containing metal centers that are formally in the +2 oxidation state, have an electron count of 14, are tetra-coordinated, and are of the general formula (IV); and neutral ruthenium or osmium metal carbene complexes containing metal centers that are formally in the +2 oxidation state, have an electron count of 18, are hexa-coordinated, and are of the general formula (III)

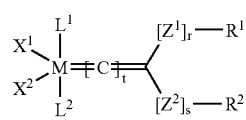

(II)

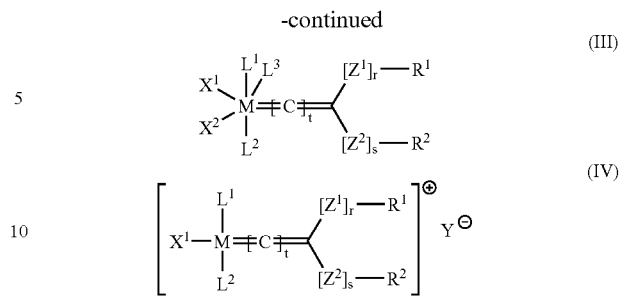

wherein $X^1$, $X^2$, $L^1$, $L^2$, n, $L^3$, $R^1$, and $R^2$ are as defined previously, r and s are independently zero or 1, t is an integer in the range of zero to 5, Y is any noncoordinating anion (e.g., a halide ion), $Z^1$ and $Z^2$ are independently selected from —O—, —S—, —$NR^2$—, —$PR^2$—, —P(=O)$R^2$—, —P($OR^2$)—, —P(=O)($OR^2$)—, —C(=O)—, —C(=O)O—, —OC(=O)—, —OC(=O)O—, —S(=O)—, or —S(=O)$_2$—, and any two or more of $X^1$, $X^2$, $L^1$, $L^2$, $L^3$, n, $Z^1$, $Z^2$, $R^1$, and $R^2$ may be taken together to form a cyclic group, e.g., a multidentate ligand, and wherein any one or more of $X^1$, $X^2$, $L^1$, $L^2$, n, $L^3$, $Z^1$, $Z^2$, $R^1$, and $R^2$ may be attached to a support. As understood in the field of catalysis, suitable solid supports may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect, if indirect, typically through a functional group on a support surface.

The transition metal complexes used as catalysts herein can be prepared by several different methods, such as those described by Schwab et al. (1996) *J. Am. Chem. Soc.* 118: 100-110, Scholl et al. (1999) *Org. Lett.* 6:953-956, Sanford et al. (2001) *J. Am. Chem. Soc.* 123:749-750, U.S. Pat. Nos. 5,312,940 and 5,342,909. Also see U.S. Pat. Publication No. 2003/0055262 to Grubbs et al. for "Group 8 Transition Metal Carbene Complexes as Enantioselective Olefin Metathesis Catalysts," International Patent Publication No. WO 02/079208 to Grubbs et al. for "One-Pot Synthesis of Group 8 Transition Metal Carbene Complexes Useful as Olefin Metathesis Catalysts," commonly assigned herewith to the California Institute of Technology. Preferred synthetic methods are described in International Patent Publication No. WO 03/11455A1 to Grubbs et al. for "Hexacoordinated Ruthenium or Osmium Metal Carbene Metathesis Catalysts," published Feb. 13, 2003.

III. The Cross-Metathesis Reaction

The transition metal complexes described in the foregoing section are used herein to catalyze an olefin metathesis reaction to synthesize olefins directly substituted with an electron-withdrawing group and substituted with at least one additional substituent. The first olefinic reactant has the structure of formula (IX)

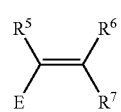

wherein the various substituents are as follows:

E is an electron-withdrawing group, which, as will be appreciated by those of ordinary skill in the art, is a group that has greater electronegativity than the carbon atom to which it is bound. In general, this means that E is more electron-withdrawing than a hydrogen atom. Accordingly, representative electron-withdrawing substituents include, without limitation, halo, cyano, $C_1$-$C_{20}$ haloalkyl (preferably $C_1$-$C_{12}$ haloalkyl, more preferably $C_1$-$C_6$ haloalkyl), $C_1$-$C_{20}$ alkylsulfonyl (preferably $C_1$-$C_{12}$ alkylsulfonyl, more preferably $C_1$-$C_6$ alkylsulfonyl), $C_5$-$C_{24}$ arylsulfonyl (preferably $C_5$-$C_{14}$ arylsulfonyl), carboxyl, $C_5$-$C_{24}$ aryloxy (preferably $C_5$-$C_{14}$ aryloxy), $C_1$-$C_{20}$ alkoxy (preferably $C_1$-$C_{12}$ alkoxy, more preferably $C_1$-$C_6$ alkoxy), $C_6$-$C_{24}$ aryloxycarbonyl (preferably $C_6$-$C_{14}$ aryloxycarbonyl), $C_1$-$C_{20}$ alkoxycarbonyl (preferably $C_1$-$C_{12}$ alkoxycarbonyl, more preferably $C_1$-$C_6$ alkoxycarbonyl), $C_6$-$C_{24}$ arylcarbonyl (preferably $C_6$-$C_{14}$ arylcarbonyl), $C_1$-$C_{20}$ alkylcarbonyl (preferably $C_1$-$C_{12}$ alkylcarbonyl, more preferably $C_1$-$C_6$ alkylcarbonyl), formyl, nitro, quaternary amino (including alkyl- and aryl-substituted amino), sulfhydryl, $C_1$-$C_{20}$ alkylthio (preferably $C_1$-$C_{12}$ alkylthio, more preferably $C_1$-$C_6$ alkylthio), $C_5$-$C_{24}$ arylthio (preferably $C_5$-$C_{14}$ arylthio), hydroxyl, $C_5$-$C_{24}$ aryl (preferably $C_5$-$C_{14}$ aryl), $C_1$-$C_{20}$ alkyl (preferably $C_1$-$C_{12}$ alkyl, more preferably $C_1$-$C_6$ alkyl), any of which may be substituted and/or heteroatom-containing. Cyano groups are of particular interest herein.

$R^5$, $R^6$, and $R^7$ are independently selected from the group consisting of hydrogen, $-(Z)_m$-Fn, hydrocarbyl, substituted hydrocarbyl, heteroatom-containing hydrocarbyl, and substituted heteroatom-containing hydrocarbyl, and, if substituted hydrocarbyl or substituted heteroatom-containing hydrocarbyl, wherein one or more of the substituents may be $-(Z)_m$-Fn. In a preferred embodiment, $R^5$ is hydrogen or substituted and/or heteroatom-containing $C_1$-$C_{12}$ hydrocarbyl, e.g., $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, or substituted $C_6$-$C_{16}$ heteroaralkyl, and $R^6$ and $R^7$ are hydrogen. In a more preferred embodiment, $R^5$ is hydrogen, $C_1$-$C_{12}$ alkyl, or $C_6$-$C_{16}$ aralkyl, and, most preferably, $R^5$ is hydrogen.

Fn is a functional group as defined earlier herein, with exemplary Fn groups including, without limitation, halide, hydroxyl, sulfhydryl, $C_1$-$C_{20}$ alkoxy, $C_5$-$C_{24}$ aryloxy, $C_6$-$C_{24}$ aralkyloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl)-N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$, alkyl)-substituted amino, mono-($C_5$-$C_{24}$ aryl)-substituted amino, di-($C_5$-$C_{24}$ aryl)-substituted amino, ($C_1$-$C_{20}$ alkyl)($C_5$-$C_{24}$ aryl)-substituted amino, $C_2$-$C_{20}$ alkylamido, $C_6$-$C_{24}$ arylamido, imino, $C_2$-$C_{20}$ alkylimino, $C_6$-$C_{24}$arylimino, nitro, nitroso, sulfo, sulfonato, $C_1$-$C_{20}$ alkylthio, $C_5$-$C_{24}$ arylthio, $C_1$-$C_{20}$ alkylsulfinyl, $C_5$-$C_{24}$ arylsulfinyl, $C_1$-$C_{20}$ alkylsulfonyl, $C_5$-$C_{24}$ arylsulfonyl, boryl, borono, boronato, phosphono, phosphonato, phosphinato, phospho, and phosphino, any of which may be further substituted, if the functional group allows, with an additional functional group and/or at least one hydrocarbyl moiety generally selected from $C_1$-$C_{20}$ alkyl (preferably $C_1$-$C_{12}$ alkyl, more preferably $C_1$-$C_6$ alkyl), $C_2$-$C_{20}$ alkenyl (preferably $C_2$-$C_{12}$ alkenyl, more preferably $C_2$-$C_6$ alkenyl), $C_2$-$C_{20}$ alkynyl (preferably $C_2$-$C_2$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

Z is a hydrocarbylene (e.g., $C_1$-$C_{20}$ alkylene, $C_2$-$C_{20}$ alkenylene, $C_2$-$C_{20}$ alkynylene, $C_5$-$C_{24}$ arylene, $C_6$-$C_{24}$ alkarylene, or $C_6$-$C_{24}$ aralkylene), substituted hydrocarbylene (e.g., substituted $C_1$-$C_{20}$ alkylene, $C_2$-$C_{20}$ alkenylene, $C_2$-$C_{20}$ alkynylene, $C_5$-$C_{24}$ arylene, $C_6$-$C_{24}$ alkarylene, or $C_6$-$C_{24}$ aralkylene), heteroatom-containing hydrocarbylene (e.g., $C_1$-$C_{20}$ heteroalkylene, $C_2$-$C_{20}$ heteroalkenylene, $C_2$-$C_{20}$ heteroalkynylene, $C_5$-$C_{24}$heteroarylene, heteroatom-containing $C_6$-$C_{24}$ aralkylene, or heteroatom-containing $C_6$-$C_{24}$ alkarylene), or substituted heteroatom-containing hydrocarbylene (e.g., substituted $C_1$-$C_{20}$ heteroalkylene, substituted $C_2$-$C_{20}$ heteroalkenylene, substituted $C_2$-$C_{20}$ heteroalkynylene, substituted $C_5$-$C_{24}$ heteroarylene, substituted heteroatom-containing $C_6$-$C_{24}$ aralkylene, or substituted heteroatom-containing $C_6$-$C_{24}$ alkarylene). Preferred Z linkages are $C_1$-$C_{12}$ alkylene, optionally substituted and/or heteroatom-containing, and particularly preferred Z linkages are $C_1$-$C_6$ alkylene. The functional group will generally not be directly bound to the olefinic carbon through a heteroatom containing one or more lone pairs of electrons, e.g., an oxygen, sulfur, nitrogen or phosphorus atom; with such functional groups, there will normally be an intervening linkage Z, i.e., m is 1.

The reaction partner, i.e., the second olefinic reactant, has a molecular structure given by formula (X)

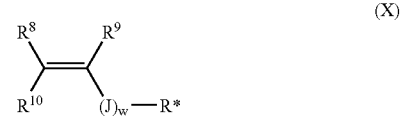

wherein w is zero or 1, J is a linking group and is defined as for Z, R* is a nonhydrogen substituent, e.g., hydrocarbyl, substituted hydrocarbyl, heteroatom-containing hydrocarbyl, substituted heteroatom-containing hydrocarbyl, or Fn, and $R^8$, $R^9$, and $R^{10}$ are hydrogen, hydrocarbyl, substituted hydrocarbyl, heteroatom-containing hydrocarbyl, substituted heteroatom-containing hydrocarbyl, $-(Z)_m$-Fn, or $-(J)_w$-R*.

In a preferred embodiment:
either (1) $R^8$ and $R^{10}$ are hydrogen, or (2) $R^8$ and $R^9$ are hydrogen and $R^{10}$ is either hydrogen or $-(J)_w$-R*;

J is $C_1$-$C_6$ alkylene, substituted $C_1$-$C_6$ alkylene, $C_1$-$C_6$ heteroalkylene, or substituted $C_1$-$C_6$ heteroalkylene, and is preferably $C_1$-$C_6$ alkylene; and R* is selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ aralkyl, substituted $C_6$-$C_{24}$ aralkyl, $C_6$-$C_{24}$ heteroaralkyl, and substituted $C_6$-$C_{24}$ heteroaralkyl, hydroxyl, sulfhydryl, protected hydroxyl, protected sulfhydryl, $C_1$-$C_{20}$ alkoxy, $C_5$-$C_{24}$ aryloxy, $C_6$-$C_{24}$ aralkyloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl)-N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$alkyl)-substituted amino, di-($C_1$-$C_{20}$alkyl)-substituted amino, mono-($C_5$-$C_{24}$aryl)-substituted amino, di-($C_5$-$C_{24}$aryl)-substituted amino, di-N—($C_1$-$C_{20}$ alkyl)-N—($C_5$-$C_{24}$ aryl)-substituted amino, $C_2$-$C_{20}$ alkylamido, $C_6$-$C_{24}$ arylamido, imino, $C_2$-$C_{20}$ alkylimino, $C_6$-$C_{24}$ arylimino, nitro, nitroso, sulfo, sulfonato, $C_1$-$C_{20}$ alkylthio, $C_5$-$C_{24}$ arylthio, $C_1$-$C_{20}$ alkylsulfinyl, $C_5$-$C_{24}$arylsulfinyl, $C_1$-$C_{20}$ alkylsulfonyl, $C_5$-$C_{24}$ arylsulfonyl, boryl, borono, boronato, phosphono, phosphonato, phosphinato, phospho, and phosphino.

In a more preferred embodiment, J is $C_1$-$C_3$ alkylene, e.g., methylene, and R* is selected from hydroxyl, sulfhydryl, protected hydroxyl, protected sulfhydryl, $C_1$-$C_{12}$ alkoxy, $C_5$-$C_{14}$ aryloxy, $C_6$-$C_{14}$ aralkyloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, di-($C_1$-$C_{12}$ alkyl)-substituted carbamoyl, di-N—($C_1$-$C_{12}$ alkyl)-N—($C_5$-$C_{14}$ aryl)-substituted carbamoyl, mono-($C_5$-$C_{14}$ aryl)-substituted carbamoyl, di-($C_6$-$C_{14}$ aryl)-substituted carbamoyl, formyl, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_{14}$ aryl)-substituted amino, di-N—($C_1$-$C_{20}$ alkyl)-N—($C_5$-$C_{24}$ aryl)-substituted amino, $C_2$-$C_{12}$ alkylamido, $C_6$-$C_{14}$arylamido, nitro, $C_1$-$C_{12}$ alkylthio, and $C_5$-$C_{14}$ arylthio. Most typical R* substituents are hydroxyl, protected hydroxyl, $C_1$-$C_6$ alkoxy, $C_5$-$C_{14}$ aryloxy, $C_6$-$C_{14}$ aralkyloxy, $C_2$-$C_6$ alkylcarbonyl, $C_6$-$C_{14}$ arylcarbonyl, halocarbonyl, formyl di-($C_1$-$C_6$ alkyl)-substituted amino, di-($C_5$-$C_{14}$aryl)-substituted amino, $C_1$-$C_6$ alkylthio, and $C_5$-$C_{14}$ arylthio.

Accordingly, one representative reaction of the invention, wherein $R^6$, $R^7$, $R^8$, and $R^{10}$ are hydrogen, is illustrated in Scheme 1:

Scheme 1:

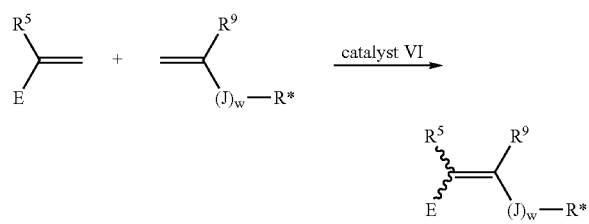

Another representative reaction of the invention, wherein $R^5$, $R^6$, $R^7$, $R^8$, and $R^9$ are hydrogen and $R^{10}$ is -(J)$_w$-R*, is illustrated in Scheme 2:

Scheme 2:

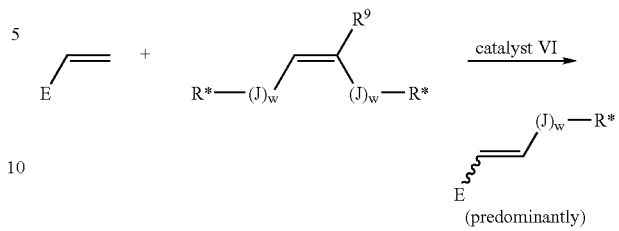

The capability of the method of the invention with respect to synthesis of such substituted olefins, wherein an electron-withdrawing substituent is directly bound to an olefinic carbon atom, is illustrated in Example 4 using several types of olefinic reactants and the ruthenium catalysts (2), (3), and (4)

(2)

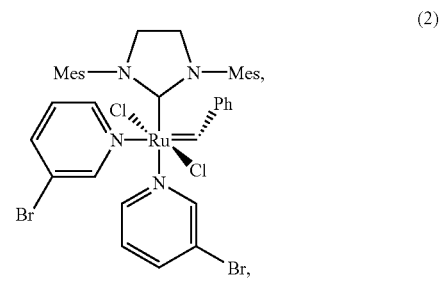

(3)

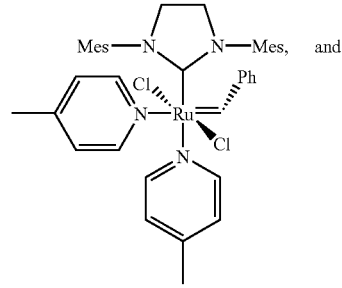

and (4)

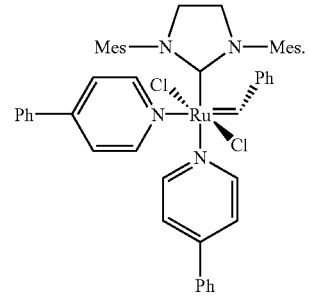

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

Experimental:

Manipulation of organometallic compounds was performed using standard Schlenk techniques under an atmosphere of dry argon or in a nitrogen-filled Vacuum Atmospheres drybox ($O_2<2$ ppm). NMR spectra were recorded on a Varian Inova (499.85 MHz for $^1H$; 202.34 MHz for $^{31}P$; 125.69 MHz for $^{13}C$) or a Varian Mercury 300 (299.817 for $^1H$; 121.39 MHz for $^{31}P$; 74.45 MHz for $^{13}C$). $^{31}P$ NMR spectra were referenced using $H_3PO_4$ ($\delta=0$ ppm) as an external standard. UV-vis spectra were recorded on an HP 8452A diode-array spectrophotometer.

Materials and methods: All solvents were dried by passage through solvent purification columns. Pyridine was dried by vacuum transfer from $CaH_2$.

EXAMPLE 1

Synthesis of $(IMesH_2)(C_5H_4BrN)_2(Cl_2)=CHPh$ (2):

Complex 1 (($IMesH_2)(PCy_3)_2(Cl_2)=CHPh$) (2.0 g), prepared according to literature procedures,

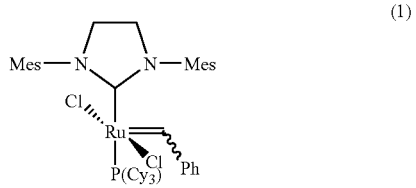

(1)

was dissolved in toluene (10 mL), and 3-bromopyridine (1.50 grams, 4 mol equivalents) was added. The reaction flask was purged with argon and the reaction mixture was stirred for approximately 12 hours at about 20° C. to about 25° C. during which time a color change from dark purple to light green was observed. The reaction mixture was transferred into 75 mL of cold (about 0° C.) pentane, and a light green solid precipitated. The precipitate was filtered, washed with 4×20 mL of cold pentane, and dried under vacuum to afford $(IMesH_2)(C_5H_4BrN)_2(Cl)_2Ru=CHPh$ 2 as a light green powder (1.8 grams, 86% yield).

EXAMPLE 2

Synthesis of $(IMesH_2)(C_6H_7N)_2(Cl_2)=CHPh$ (3):

Complex 1 (2.0 grams) was dissolved in toluene (10 mL), and 4-methylpyridine (0.88 grams, 4 mol equivalents) was added. The reaction flask was purged with argon and the reaction mixture was stirred for approximately 12 hours at about 20° C. to about 25° C. during which time a color change from dark purple to light green was observed. The reaction mixture was transferred into 75 mL of cold (about 0° C.) pentane, and a light green solid precipitated. The precipitate was filtered, washed with 4×20 mL of cold pentane, and dried under vacuum to afford $(IMesH_2)(C_6H_7N)_2Ru=CHPh$ 3 as a light green powder (1.5 grams, 84% yield).

EXAMPLE 3

Synthesis of $(IMesH_2)(C_{11}H_9N)_2(Cl_2)=CHPh$ (4):

Complex 1 (2.0 grams) was dissolved in toluene (10 mL), and 4-phenylpyridine (1.50 grams, 4 mol equivalents) was added. The reaction flask was purged with argon and the reaction mixture was stirred for approximately 12 hours at about 20° C. to about 25° C. during which time a color change from dark purple to dark green was observed. The reaction mixture was transferred into 75 mL of cold (about 0° C.) pentane, and a dark green solid precipitated. The precipitate was filtered, washed with 4×20 mL of cold pentane, and dried under vacuum to afford $(IMesH_2)(C_{11}H_9N)_2(Cl)_2Ru=CHPh$ 4 as a dark green powder (2.0 grams, 97% yield).

$^1H$ NMR (500 MHz, $CD_2Cl_2$): $\delta$ 19.23 (s, 1H, CHPh), 8.74 (br. s, 2H, pyridine), 7.91 (br. s, 2H, pyridine), 7.70–7.08 (multiple peaks, 19H, ortho CH, para CH, meta CH, pyridine), 6.93 (br. S, 2H, Mes CH) 6.79 (br. s, 2H, Mes CH), 4.05 (br. s, 4H, $NCH_2CH_2N$), 2.62–2.29 (multiple peaks, 18H, Mes $CH_3$).

EXAMPLE 4

Cross-Metathesis (CM) Reactions:

General procedure: Cross-metathesis reactions were conducted with 1.0 or 2.5 mol % of catalyst (1), (2), or (3) in a reaction with acrylonitrile (1 equivalent) and either an α-terminal olefin or a 1,2-disubstituted olefin (2.5 equivalents) in methylene chloride at room temperature or 40° C. for 12 hours to generate the di- or trisubstituted CM product. The specific conditions for each reaction are set forth in Table 1. In general, it should be noted that the CM reaction will generally be carried out in a solvent at a temperature in the range of about 20° C. to about 80° C., optimally about 25° C. to about 45° C., with about 0.1 mol % to about 5 mol %, optimally about 0.5 mol % to about 3.5 mol % catalyst. It should be noted that depending on the substitution of the pyridine ligands, high Z-olefin selectivity (>10:1 Z:E) also can be achieved.

TABLE 1

Cross Metathesis of Acrylonitrile

| cross partner | mol % catalyst | mol % catalyst | temp ° C. | yield (%) | E:Z | R |
|---|---|---|---|---|---|---|
|  | 2 | 2.5 | 40° C. | 81 | 1.1:1 | OTBS |
|  | 2 | 1 | 40° C. | 76 | 1:1 | OTBS |
|  | 2 | 2.5 | 40° C. | 71 | 1:1.7 | OBn |
|  | 2 | 2.5 | 40° C. | 67 | 1:1.8 | Ph |
|  | 2 | 2.5 | rt | 36 | 1:1 | Ph |
|  | 3 | 2.5 | 40° C. | 22 | 1:>10 | Ph |
|  | 4 | 2.5 | 40° C. | 29 | 1:1.8 | Ph |

We claim:

1. A method for synthesizing an olefin directly substituted with an electron-withdrawing group and substituted with at least one additional substituent, comprising contacting (a) a first olefinic reactant directly substituted with an electron-withdrawing group with (b) a second olefinic reactant substituted with a different substituent in the presence of (c) a catalyst composed of a Group 8 transition metal alkylidene complex under conditions and for a time period effective to allow cross-metathesis to occur, wherein the catalyst contains two anionic ligands, a carbene ligand, and one or two electron-donating heterocyclic ligands, and wherein the carbene ligand is different from the one or two electron-donating heterocyclic ligands, and wherein the transition metal alkylidene complex has the structure of formula (VI)

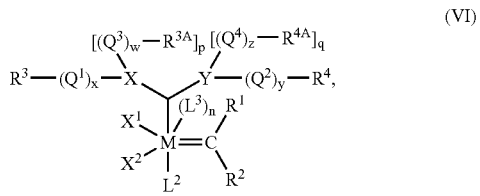

(VI)

wherein:
M is the Group 8 transition metal;
n is zero or 1;
$X^1$ and $X^2$ are the anionic ligands;
$L^2$ and $L^3$ are the electron-donating heterocyclic ligands, or may be taken together to form a single bidentate electron-donating heterocyclic ligand, provided that $L^2$ and $L^3$ are selected from nitrogen-containing heterocycles, sulfur-containing heterocycles, and oxygen-containing heterocycles;
$R^1$ and $R^2$ are independently selected from hydrogen, hydrocarbyl, substituted hydrocarbyl, heteroatom-containing hydrocarbyl, substituted heteroatom-containing hydrocarbyl, and functional groups, or may be taken together to form a vinylidene moiety;
X and Y are heteroatoms selected from N, O, S, and P;
p is zero when X is O or S, and p is 1 when X is N or P;
q is zero when Y is O or S, and q is 1 when Y is N or P;
$Q^1$, $Q^2$, $Q^3$, and $Q^4$ are independently selected from hydrocarbylene, substituted hydrocarbylene, heteroatom-containing hydrocarbylene, substituted heteroatom-containing hydrocarbylene, and —(CO)—, and further wherein two or more substituents on adjacent atoms within Q may be linked to form an additional cyclic group;
w, x, y, and z are independently zero or 1; and
$R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl,
wherein any two or more of $X^1$, $X^2$, $L^2$, $L^3$, $R^1$, and $R^2$ can be taken together to form a cyclic group, and further wherein any one or more of $X^1$, $X^2$, $L^2$, $L^3$, $R^1$, and $R^2$ may be attached to a support.

2. The method of claim 1, wherein the electron-withdrawing group is selected from halo, cyano, $C_1$-$C_{20}$ haloalkyl, $C_1$-$C_{20}$ alkylsulfonyl, $C_5$-$C_{24}$ arylsulfonyl, carboxyl, $C_5$-$C_{24}$ aryloxy, $C_1$-$C_{20}$ alkoxy, $C_6$-$C_{24}$ aryloxycarbonyl, $C_2$-$C_{20}$ alkoxycarbonyl, $C_6$-$C_{24}$ arylcarbonyl, $C_2$-$C_{20}$ alkylcarbonyl, formyl, nitro, quaternary amino, sulfhydryl, $C_1$-$C_{20}$ alkylthio, $C_5$-$C_{24}$ arylthio, hydroxyl, $C_5$-$C_{24}$ aryl, and $C_1$-$C_{20}$ alkyl, any of which may be substituted and/or heteroatom-containing.

3. The method of claim 2, wherein the electron-withdrawing group is selected from halo, cyano, $C_1$-$C_{12}$ haloalkyl, $C_1$-$C_{12}$ alkylsulfonyl, $C_5$-$C_{14}$ arylsulfonyl, carboxyl, $C_5$-$C_{14}$ aryloxy, $C_1$-$C_{12}$ alkoxy, $C_6$-$C_{14}$ aryloxycarbonyl, $C_2$-$C_{12}$ alkoxycarbonyl, $C_6$-$C_{14}$ arylcarbonyl, $C_2$-$C_{12}$ alkylcarbonyl, formyl, nitro, quaternary amino, sulfhydryl, $C_1$-$C_{12}$ alkylthio, $C_5$-$C_{24}$ arylthio, hydroxyl, $C_5$-$C_{24}$ aryl, and $C_1$-$C_{12}$ alkyl, any of which may be substituted and/or heteroatom-containing.

4. The method of claim 3, wherein the electron-withdrawing group is cyano.

5. The method of claim 1, wherein: the first olefinic reactant has the structure $CH_2$=$CER^5$ wherein E is the electron-withdrawing group and $R^5$ is hydrogen or substituted and/or heteroatom-containing $C_1$-$C_{12}$ hydrocarbyl; and the second olefinic reactant has the structure

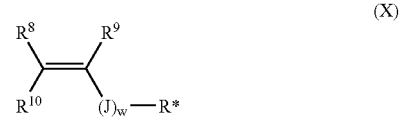

(X)

wherein w is zero or 1, J is a linking group, R* is a nonhydrogen substituent, and $R^8$, $R^9$, and $R^{10}$ are hydrogen, hydrocarbyl, substituted hydrocarbyl, heteroatom-containing hydrocarbyl, substituted heteroatom-containing hydrocarbyl, or -$(J)_w$-R*.

6. The method of claim 5, wherein $R^5$, $R^8$, and $R^{10}$ are hydrogen.

7. The method of claim 6, wherein $R^9$ is hydrogen.

8. The method of claim 7, wherein E is cyano, w is 1, J is $C_1$-$C_6$ alkylene, substituted $C_1$-$C_6$ alkylene, heteroatom-containing $C_1$-$C_6$ alkylene, and substituted heteroatom-containing $C_1$-$C_6$ alkylene, and R* is selected from hydrocarbyl, substituted hydrocarbyl, heteroatom-containing hydrocarbyl, substituted heteroatom-containing hydrocarbyl, and functional groups.

9. The method of claim 8, wherein J is $C_1$-$C_6$ alkylene and R* is selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ aralkyl, substituted $C_6$-$C_{24}$ aralkyl, $C_6$-$C_{24}$ heteroaralkyl, and substituted $C_6$-$C_{24}$ heteroaralkyl, hydroxyl, sulfhydryl, protected hydroxyl, protected sulfhydryl, $C_1$-$C_{20}$ alkoxy, $C_5$-$C_{24}$ aryloxy, $C_6$-$C_{24}$ aralkyloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl)-N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$alkyl)-substituted amino, mono-($C_5$-$C_{24}$ aryl)-substituted amino, di-($C_5$-$C_{24}$ aryl)-substituted amino, di-N—($C_1$-$C_{20}$ alkyl)-N—($C_5$-$C_{24}$ aryl)-substituted amino, $C_2$-$C_{20}$ alkylamido, $C_6$-$C_{24}$ arylamido, imino, $C_2$-$C_{20}$ alkylimino, $C_6$-$C_{24}$ arylimino, nitro, nitroso, sulfo, sulfonato, $C_1$-$C_{20}$ alkylthio, $C_5$-$C_{24}$ arylthio, $C_1$-$C_{20}$ alkylsulfinyl, $C_5$-$C_{24}$ arylsulfinyl, $C_1$-$C_{20}$ alkylsulfonyl, $C_5$-$C_{24}$ arylsulfonyl, boryl borono, boronato, phosphono, phosphonato, phosphinato, phospho, and phosphino.

10. The method of claim 8, wherein J is $C_1$-$C_3$ alkylene and R* is selected from hydroxyl, sulfhydryl, protected hydroxyl, protected sulfhydryl, $C_1$-$C_{12}$ alkoxy, $C_5$-$C_{14}$ aryloxy, $C_6$-$C_{14}$ aralkyloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, di-($C_1$-$C_{12}$ alkyl)-substituted carbamoyl, di-N—($C_1$-$C_{12}$ alkyl)-N—($C_5$-$C_{14}$ aryl)-substituted carbamoyl, mono-($C_5$-$C_{14}$ aryl)-substituted carbamoyl, di-($C_6$-$C_{14}$ aryl)-substituted carbamoyl, formyl, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_{14}$ aryl)-substituted amino, di-N—($C_1$-$C_{20}$ alkyl)-N—($C_5$l-$C_{24}$ aryl)-substituted amino, $C_2$-$C_{12}$ alkylamido, $C_6$-$C_{14}$arylamido, nitro, $C_1$-$C_{12}$ alkylthio, and $C_5$-$C_{14}$ arylthio.

11. The method of claim 10, wherein J is methylene and R* is selected from hydroxyl, protected hydroxyl, $C_1$-$C_6$ alkoxy, $C_5$-$C_{14}$ aryloxy, $C_6$-$C_{14}$ aralkyloxy, $C_2$-$C_6$ alkylcarbonyl, $C_6$-$C_{14}$ arylcarbonyl, halocarbonyl, formyl, di-($C_1$-$C_6$ alkyl)-substituted amino, di-($C_5$-$C_{14}$ aryl)-substituted amino, $C_1$-$C_6$ alkylthio, and $C_5$-$C_{14}$ arylthio.

12. The method of claim 5, wherein $R^5$, $R^8$, and $R^9$ are hydrogen and $R^{10}$ is -(J)$_w$-R*.

13. The method of claim 12, wherein E is cyano, w is 1, J is $C_1$-$C_6$ alkylene, substituted $C_1$-$C_6$ alkylene, heteroatom-containing $C_1$-$C_6$ alkylene, or substituted heteroatom-containing $C_1$-$C_6$ alkylene, and R* is selected from hydrocarbyl, substituted hydrocarbyl, heteroatom-containing hydrocarbyl, substituted heteroatom-containing hydrocarbyl, and functional groups.

14. The method of claim 13, wherein J is $C_1$-$C_6$ alkylene and R* is selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ aralkyl, substituted $C_6$-$C_{24}$ aralkyl, $C_6$-$C_{24}$ heteroaralkyl, and substituted $C_6$-$C_{24}$ heteroaralkyl, hydroxyl, sulfhydryl, protected hydroxyl, protected sulfhydryl, $C_1$-$C_{20}$ alkoxy, $C_5$-$C_{24}$ aryloxy, $C_6$-$C_{24}$ aralkyloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl)-N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$alkyl)-substituted amino, mono-($C_5$-$C_{24}$ aryl)-substituted amino, di-($C_5$-$C_{24}$ aryl)-substituted amino, di-N—($C_1$-$C_{20}$ alkyl)-N—($C_5$-$C_{24}$ aryl)-substituted amino, $C_2$-$C_{20}$ alkylamido, $C_6$-$C_{24}$ arylamido, imino, $C_2$-$C_{20}$ alkylimino, $C_6$-$C_{24}$ arylimino, nitro, nitroso, sulfo, sulfonato, $C_1$-$C_{20}$ alkylthio, $C_5$-$C_{24}$ arylthio, $C_1$-$C_{20}$ alkylsulfinyl, $C_5$-$C_{24}$ arylsulfinyl, $C_1$-$C_{20}$ alkylsulfonyl, $C_5$-$C_{24}$ arylsulfonyl, boryl, borono, boronato, phosphono, phosphonato, phosphinato, phospho, and phosphino.

15. The method of claim 14, wherein J is $C_1$-$C_3$ alkylene and R* is selected from hydroxyl, sulfhydryl, protected hydroxyl, protected sulfhydryl, $C_1$-$C_{12}$ alkoxy, $C_5$-$C_{14}$ aryloxy, $C_6$-$C_{14}$ aralkyloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, di-($C_1$-$C_{12}$ alkyl)-substituted carbamoyl, di-N—($C_1$-$C_{12}$ alkyl)-N—($C_5$-$C_{14}$ aryl)-substituted carbamoyl, mono-($C_5$-$C_{14}$ aryl)-substituted carbamoyl, di-($C_6$-$C_{14}$ aryl)-substituted carbamoyl, formyl, mono-($C_1$-$C_{12}$ alkyl)-substituted amino, di-($C_1$-$C_{12}$ alkyl)-substituted amino, mono-($C_5$-$C_{14}$aryl)-substituted amino, di-($C_5$-$C_{14}$ aryl)-substituted amino, di-N—($C_1$-$C_{20}$ alkyl)-N—($C_5$-$C_{24}$ aryl)-substituted amino, $C_2$-$C_{12}$ alkylamido, $C_6$-$C_{14}$arylamido, nitro, $C_1$-$C_{12}$ alkylthio, and $C_5$-$C_{14}$ arylthio.

16. The method of claim 15, wherein J is methylene and R* is selected from hydroxyl, protected hydroxyl, $C_1$-$C_6$ alkoxy, $C_5$-$C_{14}$ aryloxy, $C_6$-$C_{14}$ aralkyloxy, $C_2$-$C_6$ alkylcarbonyl, $C_6$-$C_{14}$ arylcarbonyl, halocarbonyl, formyl, di-($C_1$-$C_6$ alkyl)-substituted amino, di-($C_5$-$C_{14}$ aryl)-substituted amino, $C_1$-$C_6$ alkylthio, and $C_5$-$C_{14}$ arylthio.

17. The method of claim 1, wherein M is ruthenium, w, x, y, and z are zero, X and Y are N, and $R^{3,4}$ and $R^{4,4}$ are linked to form -Q-, such that the complex has the structure of formula (VIII)

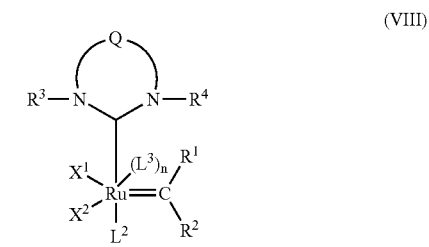

(VIII)

wherein Q is a hydrocarbylene, substituted hydrocarbylene, heteroatom-containing hydrocarbylene, or substituted heteroatom-containing hydrocarbylene linker, and further wherein two or more substituents on adjacent atoms within Q may be linked to form an additional cyclic group.

18. The method of claim 17, wherein:

$X^1$ and $X^2$ are halo;

Q is —$CR^{11}R^{12}$—$CR^{13}R^{14}$— or —$CR^{11}$=$CR^{13}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups, or wherein any two of $R^{11}$, $R^{12}$, $R^{13}$, and $R^{14}$ may be linked together to form a substituted or unsubstituted, saturated or unsaturated ring; and $R^3$ and $R^4$ are aromatic.

19. The method of claim 18, wherein:

Q is —$CR^{11}R^{12}$—$CR^{13}R^{14}$— wherein $R^{11}$, $R^{12}$, $R^{13}$, and $R^{14}$ are independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl; and $R^3$ and $R^4$ are unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide.

20. The method of claim 19, wherein $R^3$ and $R^4$ are mesityl, and $R^{11}$, $R^{12}$, $R^{13}$, and $R^{14}$ are hydrogen.

21. The method of claim 18, wherein one of $R^1$ and $R^2$ is hydrogen, and the other is selected from $C_1$-$C_{20}$ alkyl, $C_2$-$C_{20}$ alkenyl, and $C_5$-$C_{24}$ aryl, optionally substituted with one or more moieties selected from $C_1$-$C_6$ alkyl, $C_1$-$C_6$ alkoxy, and phenyl.

22. The method of claim 19, wherein one of $R^1$ and $R^2$ is hydrogen, and the other is selected from $C_2$-$C_6$ alkenyl and phenyl.

23. The method of claim 20, wherein $R^1$ is hydrogen and $R^2$ is phenyl.

24. The method of claim 1, wherein $L^2$ and $L^3$ are nitrogen-containing heterocycles.

25. The method of claim 24, wherein $L^2$ and $L^3$ are selected from pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, carbazole, any of which is optionally substituted on a non-coordinating heteroatom with a nonhydrogen substituent.

26. The method of claim 25, wherein $L^2$ and $L^3$ are selected from pyridine and substituted pyridines.

27. The method of claim 26, wherein $L^2$ and $L^3$ are selected from pyridine, 3-halopyridine, 4-methylpyridine, and 4-phenylpyridine.

28. The method of any one of claims 18, 19, 20, 21, 22, or 23, wherein n is zero and $L^2$ is selected from nitrogen-containing heterocycles, sulfur-containing heterocycles, and oxygen-containing heterocycles.

29. The method of claim 28, wherein $L^2$ is a nitrogen-containing heterocycle.

30. The method of claim 29, wherein $L^2$ is selected from pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, carbazole, any of which is optionally substituted on a non-coordinating heteroatom with a nonhydrogen substituent.

31. The method of claim 30, wherein $L^2$ is selected from pyridine and substituted pyridines.

32. The method of claim 31, wherein $L^2$ is selected from pyridine, 3-halopyridine, 4-methylpyridine, and 4-phenylpyridine.

33. The method of claim 1, wherein the catalyst has the structure of formula (II), (III), or (IV)

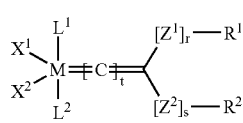

(II)

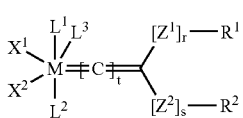

(III)

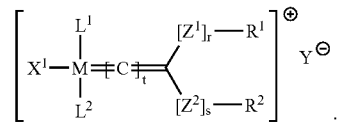

(IV)

wherein:
$X^1$ and $X^2$ are the anionic ligands;
$L^1$ is a carbene ligand;
$L^2$ and $L^3$ are the electron-donating heterocyclic ligands, or may be taken together to form a single bidentate electron-donating heterocyclic ligand;
$R^1$ and $R^2$ are independently selected from hydrogen, hydrocarbyl, substituted hydrocarbyl, heteroatom-containing hydrocarbyl, substituted heteroatom-containing hydrocarbyl, and functional groups, or may be taken together to form a vinylidene moiety;
r and s are independently zero or 1;
t is an integer in the range of zero to 5,
Y is a noncoordinating anion; and
$Z^1$ and $Z^2$ are linkages containing 1 to about 6 spacer atoms, wherein any two or more of $X^1$, $X^2$, $L^1$, $L^2$, $L^3$, $Z^1$, $Z^2$, $R^1$, and $R^2$ may be taken together to form a cyclic group, and any one or more of $X^1$, $X^2$, $L^1$, $L^2$, $L^3$, $Z^1$, $Z^2$, $R^1$, and $R^2$ may be attached to a support.

34. A method for synthesizing a substituted acrylonitrile, comprising contacting acrylonitrile with a substituted olefinic reactant in the presence of a catalyst composed of a Group 8 transition metal alkylidene complex under conditions and for a time period effective to allow cross-metathesis to occur, wherein the Group 8 transition metal is ruthenium and the catalyst has the structure of formula (VIII)

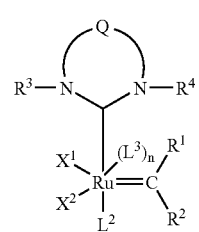

(VIII)

in which:
$X^1$ and $X^2$ are halo;
Q is —$CR^{11}R^{12}$—$CR^{13}R^{14}$— wherein $R^{11}$, $R^{12}$, $R^{13}$, and $R^{14}$ are independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl; and
one of $R^1$ and $R^2$ is hydrogen, and the other is selected from $C_2$-$C_6$ alkenyl and phenyl;
$R^3$ and $R^4$ are unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide;
n is zero or 1; and
$L^2$ and $L^3$ are selected from pyridine, 3-substituted pyridine, and 4-substituted pyridine, wherein the substituents are halo, lower alkyl, or phenyl.

35. The method of claim 34, wherein $R^{11}$, $R^{12}$, $R^{13}$, and $R^{14}$ are hydrogen, and $R^3$ and $R^4$ are mesityl.

36. The method of claim 34, wherein the substituted olefinic reactant has the structure $CH_2=CH(CH_2-R^*)$ or $CH(CH_2-R^*)=CH(CH_2-R^*)$ wherein $R^*$ is selected from hydroxyl, protected hydroxyl, $C_1$-$C_6$ alkoxy, $C_5$-$C_{14}$ aryloxy, $C_6$-$C_{14}$ aralkyloxy, $C_2$-$C_6$ alkylcarbonyl, $C_6$-$C_{14}$ arylcarbonyl, halocarbonyl, formyl, di-($C_1$-$C_6$ alkyl)-substituted amino, di-($C_5$-$C_{14}$ aryl)-substituted amino, $C_1$-$C_6$ alkylthio, and $C_5$-$C_{14}$ arylthio.

37. A method for synthesizing an olefin directly substituted with an electron-withdrawing group and substituted with at least one additional substituent, comprising contacting (a) a first olefinic reactant directly substituted with an electron-withdrawing group with (b) a second olefinic reactant substituted with a different substituent in the presence of (c) a catalyst composed of a Group 8 transition metal alkylidene complex under conditions and for a time period effective to allow cross-metathesis to occur, wherein the catalyst contains two anionic ligands, a carbene ligand, and two electron-donating heterocyclic ligands or one bidentate electron-donating heterocyclic ligand, and wherein the transition metal alkylidene complex has the structure of formula (VI)

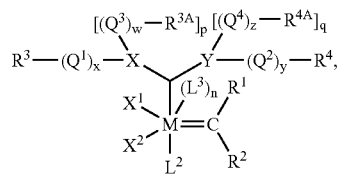

(VI)

wherein:

M is the Group 8 transition metal;

n is zero or 1;

$X^1$ and $X^2$ are the anionic ligands;

$L^2$ and $L^3$ are the electron-donating heterocyclic ligands, or may be taken together to form a single bidentate electron-donating heterocyclic ligand provided that $L^2$ and $L^3$ are selected from nitrogen-contaning heterocycles, sulfur-contaning heterocycles, and oxygen-contaning heterocycles;

$R^1$ and $R^2$ are independently selected from hydrogen, hydrocarbyl, substituted hydrocarbyl, heteroatom-containing hydrocarbyl, substituted heteroatom-containing hydrocarbyl, and functional groups, or may be taken together to form a vinylidene moiety;

X and Y are heteroatoms selected from N, O, S, and P;

p is zero when X is O or S, and p is 1 when X is N or P;

q is zero when Y is O or S, and q is 1 when Y is N or P;

$Q^1$, $Q^2$, $Q^3$, and $Q^4$ are independently selected from hydrocarbylene, substituted hydrocarbylene, heteroatom-containing hydrocarbylene, substituted heteroatom-containing hydrocarbylene, and —(CO)—, and further wherein two or more substituents on adjacent atoms within Q may be linked to form an additional cyclic group;

w, x, y, and z are independently zero or 1; and $R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl, wherein any two or more of $X^1$, $X^2$, $L^2$, $L^3$, $R^1$, and $R^2$ can be taken together to form a cyclic group, and further wherein any one or more of $X^1$, $X^2$, $L^2$, $L^3$, $R^1$, and $R^2$ may be attached to a support.

38. A method for synthesizing an olefin directly substituted with an electron-withdrawing group and substituted with at least one additional substituent, comprising contacting (a) a first olefinic reactant directly substituted with an electron-withdrawing group with (b) a second olefinic reactant substituted with a different substituent in the presence of (c) a catalyst composed of a Group 8 transition metal alkylidene complex under conditions and for a time period effective to allow cross-metathesis to occur, wherein the catalyst contains two anionic ligands, a carbene ligand, and one or two electron-donating heterocyclic ligands, and wherein the carbene ligand is different from the one or two electron-donating heterocyclic ligands, and wherein the transition metal alkylidene complex has the structure of formula (VI)

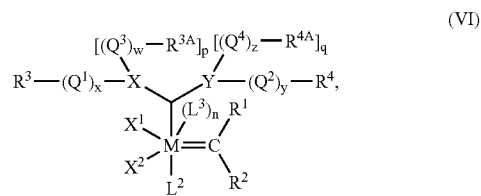

(VI)

wherein:

M is the Group 8 transition metal;

n is zero or 1;

$X^1$ and $X^2$ are the anionic ligands;

$L^2$ and $L^3$ are the electron-donating heterocyclic ligands, or may be taken together to form a single bidentate electron-donating heterocyclic ligand, provided that $L^2$ and $L^3$ are selected from nitrogen-containing heterocycles;

$R^1$ and $R^2$ are independently selected from hydrogen, hydrocarbyl, substituted hydrocarbyl, heteroatom-containing hydrocarbyl, substituted heteroatom-containing hydrocarbyl, and functional groups, or may be taken together to form a vinylidene moiety;

X and Y are heteroatoms selected from N, O, S, and P;

p is zero when X is O or S, and p is 1 when X is N or P;

q is zero when Y is O or S, and q is 1 when Y is N or P;

$Q^1$, $Q^2$, $Q^3$, and $Q^4$ are independently selected from hydrocarbylene, substituted hydrocarbylene, heteroatom-containing hydrocarbylene, substituted heteroatom-containing hydrocarbylene, and —(CO)—, and further wherein two or more substituents on adjacent atoms within Q may be linked to form an additional cyclic group;

w, x, y, and z are independently zero or 1; and $R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl, wherein any two or more of $X^1$, $X^2$, $L^2$, $L^3$, $R^1$, and $R^2$ can be taken together to form a cyclic group, and further wherein any one or more of $X^1$, $X^2$, $L^2$, $L^3$, $R^1$, and $R^2$ may be attached to a support.

39. The method of claim 38, wherein M is ruthenium, w, x, y, and z are zero, X and Y are N, and $R^{3A}$ and $R^{4A}$ are linked to form -Q-, such that the complex has the structure of formula (VIII)

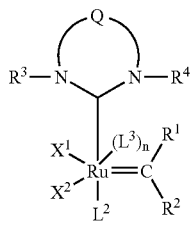

(VIII)

wherein Q is a hydrocarbylene, substituted hydrocarbylene, heteroatom-containing hydrocarbylene, or substituted heteroatom-containing hydrocarbylene linker, and further wherein two or more substituents on adjacent atoms within Q may be linked to form an additional cyclic group.

40. The method of claim 38, wherein $L^2$ and $L^3$ are selected from pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, carbazole, any of which is optionally substituted on a non-coordinating heteroatom with a nonhydrogen substibent.

41. The method of claim 40, wherein $L^2$ and $L^3$ are selected from pyridine and substituted pyridines.

42. The method of claim 41, wherein $L^2$ and $L^3$ are selected from pyridine, 3-halopyridine, 4-methylpyridine, and 4-phenylpyridine.

43. The method of claim 38, wherein M is ruthenium or osmium.

* * * * *